US00PP34386P2

(12) United States Plant Patent
Lee

(10) Patent No.: US PP34,386 P2
(45) Date of Patent: Jun. 28, 2022

(54) ***IMPATIENS* PLANT NAMED 'IMGZ0019'**

(50) Latin Name: *Impatiens interspecific*
Varietal Denomination: IMGZ0019

(71) Applicant: SYNGENTA CROP PROTECTION AG, Basel (CH)

(72) Inventor: Jaemin Lee, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/364,975

(22) Filed: Jul. 1, 2021

(51) Int. Cl.
*A01H 5/02* (2018.01)
*A01H 6/16* (2018.01)

(52) U.S. Cl.
USPC ..... Plt./317
CPC ..... *A01H 6/165* (2018.05)

(58) Field of Classification Search
USPC ..... Plt./317, 318.3
CPC ..... A01H 5/0261
See application file for complete search history.

*Primary Examiner* — Kent L Bell
(74) *Attorney, Agent, or Firm* — Dale Skalla

(57) ABSTRACT

A new *Impatiens* plant named 'IMGZ00019' particularly distinguished by the bright orange flower on medium peduncles on a medium sized well branched plant with dark green foliage.

1 Drawing Sheet

Latin name of the genus and species of the plant claimed: Interspecific *Impatiens*.

Varietal denomination: 'IMGZ0019'.

BACKGROUND OF THE NEW PLANT

The present invention comprises a new *Impatiens*, hereinafter referred to by the variety name 'IMGZ0019'.

'IMGZ0019' is a product of a planned breeding program. The new cultivar has large, flat flowers with a relatively bright orange pattern. The foliage is dark green with light green veins on the upper and lower side of the leaf. The plant is medium sized and well branched.

'IMGZ0019' originated from a hybridization made in August 2013 in a controlled breeding environment in Enkhuizen, The Netherlands.

The female parent is designated as 'k08-1410-2V' with red flower color. The male parent is designated as 'W0267-11V' and is large sized and has a white flower pattern.

The resultant seed was sown in January 2014 in a greenhouse in Enkhuizen, The Netherlands and 'IMGZ0019' was selected there as one flowering plant within the progeny of the stated cross in summer 2013. Crosses for F1 seed population were made in 2013, then seed were harvested at around the end of 2013. Harvested F1's seeds were sown in January 2014. Then, selection of 'IMGZ0019' was done in 2014.

The first act of asexual reproduction of 'IMGZ0019' was accomplished when stem vegetative cuttings were propagated from the initial selection in April 2014 in a controlled environment in Enkhuizen, The Netherlands.

BRIEF SUMMARY OF INVENTION

Horticultural examination of plants grown from cuttings of the plant initiated in July 2017 in Gilroy, Calif. USA, has demonstrated that the combination of characteristics as herein disclosed for 'IMGZ0019' are firmly fixed and are retained through successive generations of asexual reproduction.

'IMGZ0019' has been observed under different environmental conditions. The phenotype may vary significantly with variations in environment such as temperature and light intensity.

A Plant Breeder's Right for this cultivar has not yet been applied for. 'IMGZ0019' has not been made publicly available prior to the effective filing date of this application, notwithstanding any disclosure that may have been made less than one year prior to the effective filing date of this application by the inventor or another who obtained 'IMGZ0019' directly from the inventor.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

Figure 1:
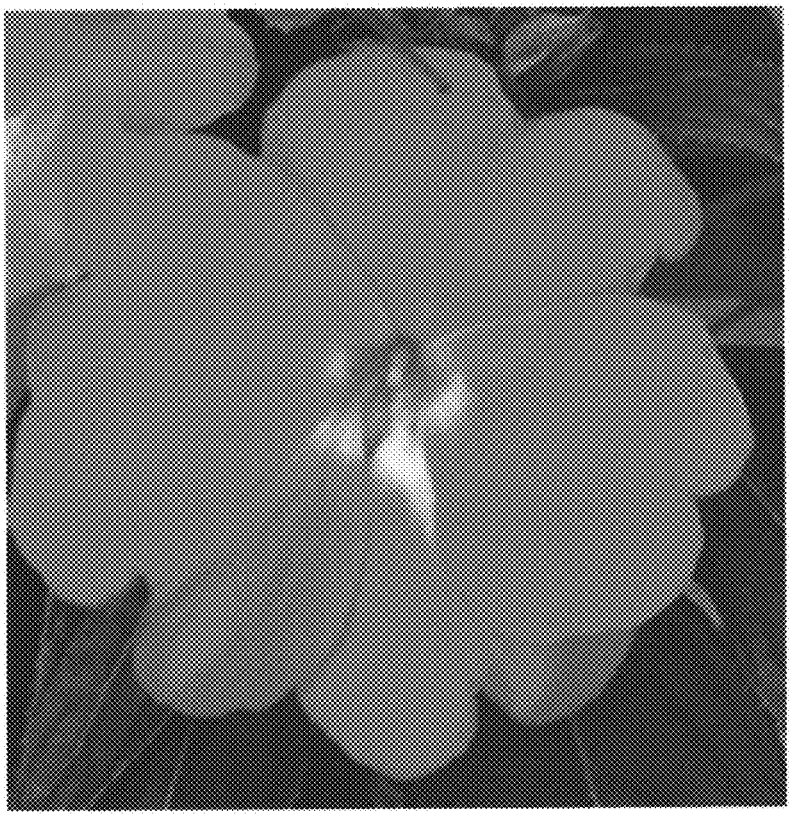
Figure 2:
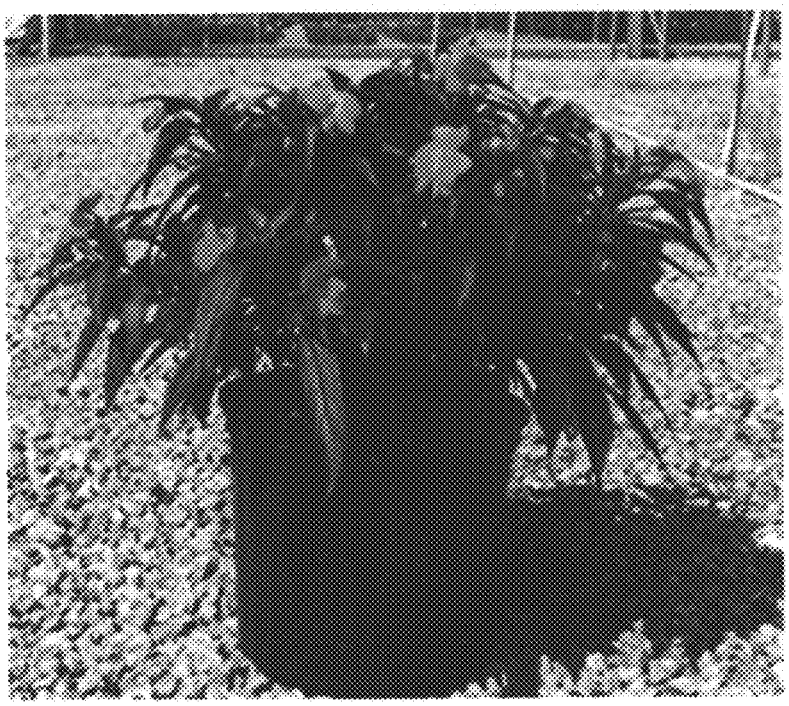

The accompanying photographic drawings show typical flower and foliage characteristics of 'IMGZ0019' with colors being as true as possible with an illustration of this type. The photographic drawings show in FIG. 1 a close-up of the flowers and in FIG. 2 a flowering plant of the new variety growing in 14 cm pot.

DETAILED BOTANICAL DESCRIPTION

The aforementioned photographs were taken in May 2021 from plants grown in a greenhouse trial in Gilroy, Calif. USA. These plants were growing in 10 cm pots and were approximately 16 weeks of age.

The plant descriptions and measurements were taken in May 2021, on 16 week old plants growing in a greenhouse in Gilroy, Calif. USA. Cuttings were stuck in week 2 for rooting, planted into 10 cm pots in week 6, and were grown, without pinching, on benches in a greenhouse, initially at a day temperature of 18° C. and night temperature of 16° C. However, day temperatures often raised above 20° C.

Color references are made to The Royal Horticultural Society Colour Chart (R.H.S.) 2001.

TABLE 1

DIFFERENCES BETWEEN THE NEW VARIETY 'IMGZ0019' AND SIMILAR PATENTED VARIETIES

| | 'IMGZ0019' | 'NG060' ('Sonic Orange') (Not patented) | 'NG149' ('Super Sonic Deep Scarlet') (Not patented) |
|---|---|---|---|
| Flower color: | Bright Orange | Orange | Scarlet |
| Flower pattern: | Small eye pattern in center | Not sharp | Not sharp |
| Habit/vigor: | Medium Vigor | Medium | Vigor |
| Branching: | More | Less | Less |

Plant:

*Form, growth and habit.*—Medium sized, mounded, well branched.

*Plant height.*—26.5 cm (without pot), 37 cm (with pot).

*Plant height (inflorescence included).*—27.0-28.0 cm (without pot).

*Plant width.*—36.0 cm.

Roots:

*Number of days to initiate roots.*—6 days at about 22 degrees C.

*Number of days to produce a rooted cutting.*—14-16 days at 22 degrees C.

*Type.*—Fibrous, free branching.

*Color.*—RHS 159A.

Foliage:

*Arrangement.*—Simple leaves, mainly in whorls.

*Young leaf, color upper surface.*—RHS 139A Dark green.

*Young leaf, color lower surface.*—Closest RHS N138B.

*Mature leaf, color upper surface.*—RHS 133A.

*Mature leaf, color lower surface.*—Closest to RHS 137C.

*Length.*—Up to 11.5 cm.

*Width.*—Up to 3.5 cm.

*Shape.*—Lanceolate.

*Base shape.*—Lanceolate.

*Apex shape.*—Acuminate.

*Margin.*—Serrulate, with short bristles.

*Texture.*—Slightly waxy and glossy on the upper surface, glabrous on both surfaces.

*Color of veins, upper surface.*—RHS 139C.

*Color of veins, lower surface.*—RHS 152C.

*Petiole color, upper side.*—RHS 147B.

*Petiole color, lower side.*—RHS 185B.

*Length.*—Up to 3.1 cm.

*Diameter.*—0.3 cm.

*Texture.*—Glabrous.

Stem:

*Color of stem.*—RHS 183B.

*Length of stem.*—About 23 cm.

*Diameter.*—1.7 cm.

*Length of internodes.*—Approximately 2.5 to 5 cm.

*Texture.*—Smooth, glabrous.

*Number of branches.*—7 main branches plus 7 side branches per main branch.

*Color of peduncle.*—RHS 46A.

*Length of peduncle.*—4.2-4.5 cm.

*Peduncle diameter.*—0.3 cm.

*Texture.*—Glabrous.

Inflorescence:

*Blooming habit.*—Continuous flowering from late spring through fall.

*Type of inflorescence.*—Solitary flowers emerge from the upper leaf nodes of the stem.

*Number of flowers per node.*—1-3 open flowers and additional buds in various stages of development.

*Quantity of flowers per plant.*—20 open flowers plus 5 (big and small) buds (10 cm pot plant in October).

*Lastingness of individual blooms on the plant.*—About 7-10 days.

*Fragrance.*—None.

Bud (just before opening):

*Color.*—RHS 43B.

*Length.*—Up to 1.8 cm.

*Width.*—Up to 1.6 cm.

*Shape.*—Ovate.

Immature flowers:

*Color of petals, upper surface.*—RHS 43B.

*Color of petals, lower surface.*—RHS 33A.

Mature flowers:

*Flower, vertical length.*—7 cm.

*Flower, horizontal width.*—7 cm.

*Flower depth.*—0.8-1.0 cm.

*Number of petals per flower.*—5 petals.

*Color of petals, upper surface.*—RHS 33A Orange.

*Color of petals, lower surface.*—RHS 40D Coral.

*Petal shape.*—Heart shaped.

*Petal apex shape.*—Broadly obcordate.

*Petal margin.*—Entire.

*Petal texture, upper surface.*—Papillose.

*Petal texture, lower surface.*—Papillose.

Calyx:

*Arrangement.*—One large sepal bearing the spur, 2 small, lateral sepals, and 1 fused keel.

*Large sepal(s).*—

*Color, visible surface.*—RHS 137B.

*Length.*—1.9 cm.

*Width.*—0.8 cm.

*Shape.*—Ovate.

*Apex shape.*—Aristate.

*Base.*—Fused with the spur.

*Margins.*—Entire.

*Texture, upper surface.*—Papillose.

*Texture, lower surface.*—Papillose.

*Lateral sepals.*—

*Color of surface.*—RHS 139D with RHS 180B.

*Length.*—1.2 cm.

*Width.*—0.7 cm.

*Shape.*—Ovate.

*Apex shape.*—Acuminate.

*Base.*—Fused.

*Margins.*—Entire.

*Texture, upper surface.*—Glabrous.

*Texture, lower surface.*—Glabrous.

*Keel color.*—From RHS 46A.

Spur:

*Color.*—RHS 46A.

*Length.*—4.7-5.0 cm.

*Diameter.*—0.3 cm at the base, 0.1 cm at tip.

Reproductive organs Androecium: 5 stamen, fused with the anthers hooded.

*Diameter of androecium.*—0.7 cm.

*Surface color.*—RHS 19D, fading towards margin.

*Pollen amount.*—FEW.

*Color of pollen.*—RHS 8D.

Gynoecium:

*Pistil.*—One, elongate.

*Pistil length.*—0.6 cm.

*Stigma color.*—RHS 19C.

*Ovary color.*—RHS 139C to RHS 144A.

*Fertility/seed set.*—Has not been observed on this hybrid.

*Disease/pest resistance.*—Has not been observed on this hybrid. However, it is downy mildew resistant.

What is claimed is:

1. A new and distinct variety of *Impatiens* plant named 'IMGZ0019' substantially as illustrated and described herein.

* * * * *